United States Patent [19]

Parekh

[11] 4,263,232

[45] Apr. 21, 1981

[54] PROCESS FOR THE MANUFACTURE OF SELECTED PHOSPHONATES

[75] Inventor: Mansukh G. Parekh, Cranston, R.I.

[73] Assignee: Ciba-Geigy Corporation, Ardsley, N.Y.

[21] Appl. No.: 55,580

[22] Filed: Jul. 9, 1979

[51] Int. Cl.$^3$ .............................................. C07F 9/40
[52] U.S. Cl. .................................................. 260/989
[58] Field of Search ......................................... 260/989

[56] References Cited

U.S. PATENT DOCUMENTS

| | | | |
|---|---|---|---|
| 3,790,648 | 2/1974 | Schmidt et al. | 260/970 |
| 3,931,360 | 1/1976 | Giolito | 260/989 |
| 3,931,361 | 1/1976 | Jaffe et al. | 260/989 |

OTHER PUBLICATIONS

Obtemperanskaya, et al., "Chem. Abs.", vol. 85, (1976), 201768k.

*Primary Examiner*—Anton H. Sutto
*Attorney, Agent, or Firm*—Luther A. R. Hall

[57] ABSTRACT

The treatment of a crude reaction product with oxygenated thiourea, a selective reducing agent, allows the preparation of colorless hindered phenol phosphonate compounds which do not discolor on storage.

4 Claims, No Drawings

PROCESS FOR THE MANUFACTURE OF SELECTED PHOSPHONATES

BACKGROUND OF THE INVENTION

This invention pertains to an improved process for the preparation of hindered phenolic benzylphosphonates which are useful as antioxidant stabilizers for a host of organic substrates.

The hindered phenolic benzylphosphonates are made by the reaction of a substituted 4-hydroxybenzylamine (Mannich base) with a dialkyl phosphite in the presence of a base. This process is described in detail in U.S. Pat. No. 3,790,648, which is incorporated herein by reference.

U.S. Pat. No. 3,790,648 teaches that the reaction is carried out in the melt or in an inert organic solvent such as aromatic hydrocarbons, higher-boiling ethers or aliphatic hydrocarbons. The bases used in the process are alkali amides, alkali hydrides, alkali hydroxides, alkali alcoholates or alkali dialkylphosphites.

Following the reaction of the Mannich base and dialkyl phosphite, the reaction mixture, preferably in the melt state, is neutralized with acetic acid. The crude product obtained is then recrystallized from acetone as seen in Example 3 of U.S. Pat. No. 3,790,648.

While the product obtained by the process of U.S. Pat. No. 3,790,648 is made in good yield (up to 90%) and of acceptable purity, the use of strong base with a hindered phenolic Mannich base amine sometimes leads to the formation of small adventitious amounts of color forming bodies, presumedly due to the presence of quinoid structures, which tend to discolor the phosphonate product as prepared or to develop in the product on storage.

To overcome this practical problem, a number of reducing agents were introduced into the process in an attempt to prepare phosphonate products which not only are colorless as formed, but which do not discolor on storage. Of all the reducing agents tried only oxygenated thiourea, sold as Arolite TD Concentrate by the Arol Chemical Products Company, Newark, N.J. 07105, was effective in the instant improved process. Sodium hydrosulfite, sodium borohydride and zinc-acetic acid all were relatively ineffective in preventing the discoloration in the phosphonate product whereas the oxygenated thiourea led to colorless product which did not discolor on storage.

DETAILED DISCLOSURE

The instant invention is to an improved process for the preparation of a compound of the formula I

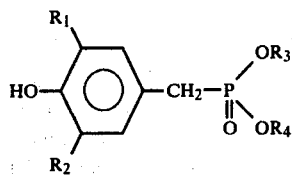

wherein $R_1$ and $R_2$ independently of one another denote a straight- or branched-chain alkyl of 1 to 8 carbon atoms or cycloalkyl of 6 to 8 carbon atoms, and $R_3$ and $R_4$ independently of one another denote a straight- or branched-chain alkyl of 1 to 22 carbon atoms, cycloalkyl of 6 to 8 carbon atoms, the —$(CH_2)_{2-12}$—S— alkyl or the —$(CH_2)_{2-12}$—O— alkyl groups wherein the alkyl group contains 1 to 18 carbon atoms, phenyl or alkylphenyl with 7 to 14 carbon atoms by the reaction of essentially stoichiometric molar amounts of a compound of formula II

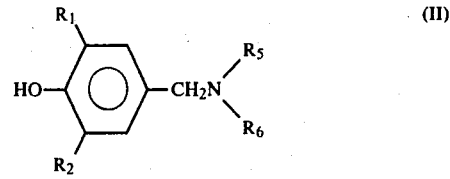

wherein $R_1$ and $R_2$ are defined as above and $R_5$ and $R_6$ independently of one another denote a straight- or branched-chain alkyl of 1 to 5 carbon atoms or together with inclusion of the nitrogen atom denote morphilino or piperidino, with a compound of formula III

wherein $R_3$ and $R_4$ are defined as above, in the presence of a base selected from the group consisting of the alkali amides, alkali hydrides, alkali hydroxides, alkali alcoholates and alkali compounds of the phosphites of formula III, followed by neutralization of the base with an organic acid, preferably acetic acid, extraction of the neutralized reaction mixture with hot dilute aqueous mineral acid, preferably hydrochloric acid, to remove all inorganic and amine salts into the aqueous layer, and isolation of the phosphonate of formula I, wherein the improvement comprises adding to the salt-free acidified crude product an effective amount of an aqueous solution of oxygenated thiourea to provide a reducing medium to reduce all color-forming bodies in the crude phosphonate product, and extracting the crude product with methanol to remove all remaining impurities and isolating the desired product.

Preferably the phosphonates made by this process are those where $R_1$ denotes methyl or branched alkyl of 3 to 4 carbon atoms, $R_2$ denotes branched alkyl of 3 to 4 carbon atoms, $R_3$ and $R_4$ denote straight- or branched-alkyl of 1 to 18 carbon atoms.

Most preferably the phosphonate made by the instant process is di-(n-octadecyl) 3,5-di-tert-butyl-4-hydroxybenzylphosphonate.

The Mannich base compounds of formula II useful in the instant process are preferably those where $R_1$ and $R_2$ are defined as above and where $R_5$ and $R_6$ are each methyl, ethyl, propyl or isopropyl, or $R_5$ and $R_6$ together with inclusion of the N atom denote piperidino.

The bases useful in this process are preferably the alkali amides or alkali alcoholates, most preferably lithium amide.

The reaction of the dialkyl phosphite of formula III with the Mannich base of formula II is most conveniently carried out in the melt in the absence of organic solvent with the concomitant evolution of a volatile dialkylamine, such as preferably dimethylamine, during the reaction which is carried out at a temperature between about 80° and 120° C. till the evolution of dialkylamine ceases. If desired, the reaction can also be carried out in the presence of an inert organic solvent such as the aromatic hydrocarbons, preferably toluene; higher-boiling ethers such as dioxane, or hydrocarbon mixtures such as ligroin.

It is known that quinones and quinoid structures often lead to strongly colored products. While the process of U.S. Pat. No. 3,790,648 minimizes the formation of such colored by-products in the instant phosphonates, the presence of even adventitious amounts of such color-forming bodies may lead to an unacceptable level of color in the instant phosphonates as prepared or upon storage thereof.

It was contemplated that the introduction of a reducing agent into the crude product upon completion of the evolution of dialkylamine, neutralization of the base and separation of all inorganic and organic salts from the crude product would overcome this seemingly small, but commercially important problem.

A large number of reducing agents including sodium hydrosulfite, sodium borohydride and zinc-acetic acid were used, but only oxygenated thiourea proved to be effective at all in eliminating the coloration of the instant phosphonate as prepared or upon storage when used in the instant process at the range of about 0.1 to 1%, preferably 0.3 to 0.6%, by weight of crude product.

It appears that oxygenated thiourea possesses some salubrious combination of properties uniquely fitted for the instant improved process. Oxygenated thiourea is described by J. Boeseken, Chemical Abstracts, 30, 6331[6](1936); ibid, 31, 1771[1](1937); ibid, 32 3758[6](1938); and ibid, 43, 1325d(1949) as thiourea dioxide or guanylsulfinic acid which may be considered as a derivative of sulfoxylic acid ($H_2SO_2$). Boeseken describes these materials as reducing agents.

The dialkyl phosphites of formula III are available as items of commerce and the Mannich bases of formula II are made from the corresponding 2,6-dialkylphenol (available as items of commerce), formaldehyde and secondary amines as described in Dutch Patent No. 68/03498.

Oxygenated thiourea or thiourea dioxide is available as Arolite TD Concentrate from the Arol Chemical Products Company, 649 Ferry Street, Newark, N.J. 07105.

Following the addition of the oxygenated thiourea to the crude product, the product is then extracted with methanol to remove all remaining impurities including the now reduced and decolorized color-forming bodies. The desired phosphonate is then isolated by conventional procedures.

The following Examples illustrate the invention

EXAMPLE 1

Di(n-octadecyl) 3,5-Di-tert-butyl-4-hydroxybenzylphosphonate.

In a 1-liter round-bottomed 3-necked flask fitted with a stirrer, nitrogen inlet tube, thermometer and vacuum line was added 94.6 grams (0.164 mole) of n-dioctadecyl phosphite and 42.5 grams (0.162 mole) of 3,5-di-tert-butyl-4-hydroxybenzyldimethylamine. The materials are mixed and heated to 60° C. to form a homogenous melt under a blanket of nitrogen. To this melt was then added 1.3 gram (0.06 mole) of lithium amide. The temperature was raised slowly with the evolution of dimethylamine beginning at about 80° C. The temperature was held in the range of about 103° to 108° C. for about 3.5 hours or till the evolution of dimethylamine ceased.

The reaction mixture was then cooled to about 50° C. and 4.6 grams of glacial acetic acid was added to neutralize the base present. The neutralized reaction mixture was then extracted with 110 grams of 10% aqueous hydrochloric acid at 82°-87° C. to remove the inorganic and organic salts in the aqueous layer.

To the non-aqueous layer containing essentially the crude phosphonate product was then added 0.6 grams of oxygenated thiourea (Arolite TD Concentrate) in 10 grams of water. After stirring the crude product with the aqueous oxygenated thiourea solution for 30 minutes at 82°-87° C., the aqueous layer was separated. The resulting organic layer was extracted with 140 ml of methanol to remove all remaining impurities in the aqueous methanol layer.

The desired phosphonate was isolated by stripping residual methanol from the non-aqueous layer under water pump vacuum. The phosphonate was obtained as a white product in a yield of 110.8 grams (85% of theory) as a white powder melting at 56°-57° C.

This product did not discolor on storage.

EXAMPLE 2

When the general procedure of Example 1 is used, other phosphonates of formula I are formed as seen below:

| Compound Formula III | Compound Formula II | Compound Formula I |
|---|---|---|
| dilauryl phosphite | 3,5-di-tert-butyl-4-hydroxybenzyl-diethylamine | dilauryl 3,5-di-tert-butyl-4-hydroxy-benzylphosphonate |
| di-n-octadecyl phosphite | N-(3-methyl-5-tert-butyl-4-hydroxybenzyl)-piperidine | di-(n-octadecyl) 3-methyl-5-tert-butyl-4-hydroxybenzyl-phosphonate |
| dilauryl phosphite | 3-methyl-5-tert-butyl-4-hydroxy-benzyldimethylamine | dilauryl 3-methyl-5-tert-butyl-4-hydroxybenzyl-phosphonate |

What is claimed is:

1. An improved process for the preparation of a compound of formula I

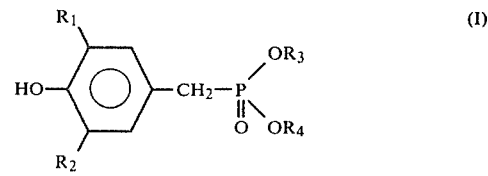

wherein $R_1$ and $R_2$ independently of one another denote a straight- or branched-chain alkyl of 1 to 8 carbon atoms or cycloalkyl of 6 to 8 carbon atoms, and $R_3$ and $R_4$ independently of one another denote a straight- or branched-chain alkyl of 1 to 22 carbon atoms, cycloalkyl of 6 to 8 carbon atoms, the $-(CH_2)_{2-12}-S-$alkyl or the $-(CH_2)_{2-12}-O-$alkyl group wherein the alkyl group contains 1 to 18 carbon atoms, phenyl or alkylphenyl with 7 to 14 carbon atoms by the reaction of essentially stoichiometric molar amounts of a compound of formula II

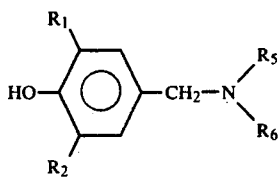

wherein $R_1$ and $R_2$ are defined as above and $R_5$ and $R_6$ independently of one another denote a straight- or branched-chain alkyl of 1 to 5 carbon atoms or together with inclusion of the nitrogen atom denote morphilino or piperidino, with a compound of the formula III

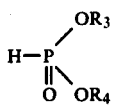

wherein $R_3$ and $R_4$ are defined as above, in the presence of a base selected from the group consisting of the alkali amides, alkali hydrides, alkali hydroxides, alkali alcoholates and alkali compounds of the phosphites of formula III, followed by neutralization of the base with an organic acid, extraction of the neutralized reaction mixture with hot dilute aqueous mineral acid to remove all inorganic and amine salts into the aqueous layer and isolation of the phosphonate of formula I, wherein the improvement comprises adding to the salt-free acidified crude product an effective amount of an aqueous solution of oxygenated thiourea to provide a reducing medium to reduce all color-forming bodies in the crude phosphonate product, and extracting the crude product with methanol to remove all remaining impurities and isolating the desired product.

2. A process according to claim 1 wherein $R_1$ denotes methyl or branched alkyl of 3 to 4 carbon atoms, $R_2$ denotes branched alkyl of 3 to 4 carbon atoms, $R_3$ and $R_4$ denote straight- or branched-chain alkyl of 1 to 18 carbon atoms, and $R_5$ and $R_6$ are each methyl, ethyl, propyl or isopropyl, or $R_5$ and $R_6$ together with inclusion of the N atom denote piperidino.

3. The process according to claim 1 to make di-(n-octadecyl) 3,5-di-tert-butyl-4-hydroxybenzyl-phosphonate.

4. A process according to claim 1 wherein from about 0.1 to about 1% by weight of crude product of oxygenated thiourea is added.

* * * * *